(12) United States Patent
Hogan

(10) Patent No.: US 6,569,191 B1
(45) Date of Patent: May 27, 2003

(54) SELF-EXPANDING STENT WITH ENHANCED RADIAL EXPANSION AND SHAPE MEMORY

(75) Inventor: James T. Hogan, Blue Bell, PA (US)

(73) Assignee: Bionx Implants, Inc., Blue Bell, PA (US)

( * ) Notice: Subject to any disclaimer, the term of this patent is extended or adjusted under 35 U.S.C. 154(b) by 0 days.

(21) Appl. No.: 09/626,638

(22) Filed: Jul. 27, 2000

(51) Int. Cl.⁷ .................................................. A61F 2/06
(52) U.S. Cl. ........................ 623/1.11; 623/1.32; 623/1.2
(58) Field of Search ............................... 623/1.11, 1.12, 623/1.13–1.23, 1.32, 1.33, 1.38, 1.44, 1.47, 1.5, 1.51, 1.53, 1.54

(56) References Cited

U.S. PATENT DOCUMENTS

| | | | |
|---|---|---|---|
| 1,205,743 A | | 7/1966 | Didcott |
| 4,655,751 A | | 4/1987 | Wallsten .................... 623/1 |
| 4,954,126 A | * | 9/1990 | Wallstén .................. 623/1.11 |
| 5,545,208 A | | 8/1996 | Wolff et al. ................... 623/1 |
| 5,591,222 A | | 1/1997 | Susawa et al. ................ 623/1 |
| 5,670,161 A | * | 9/1997 | Healy et al. ................ 128/898 |
| 5,733,327 A | * | 3/1998 | Igaki et al. ................. 623/1.5 |
| 5,766,204 A | | 6/1998 | Porter et al. ............... 606/198 |
| 5,997,468 A | * | 12/1999 | Wolff et al. ............... 623/1.11 |
| 6,015,432 A | * | 1/2000 | Rakos et al. ................ 623/1.5 |
| 6,161,399 A | * | 12/2000 | Jayaraman ................. 623/1.5 |
| 6,192,944 B1 | * | 2/2001 | Greenhalgh ................. 139/34 |
| 6,217,609 B1 | * | 4/2001 | Haverkost ................ 623/1.22 |
| 6,290,731 B1 | * | 9/2001 | Solovay et al. .......... 623/1.35 |
| 6,336,937 B1 | * | 1/2002 | Vonesh et al. ............ 623/1.13 |
| 6,348,066 B1 | * | 2/2002 | Pinchuk et al. ........... 606/198 |

FOREIGN PATENT DOCUMENTS

EP    0894505 A2    2/1999

* cited by examiner

Primary Examiner—Michael J. Milano
Assistant Examiner—Tan-Uyen (Jackie) T. Ho
(74) Attorney, Agent, or Firm—Synnestvedt & Lechner LLP

(57) ABSTRACT

The invention comprises a bioabsorbable radially self-expanding stent with one or more supplemental apparatus or methods for achieving the desired final resting diameter of the stent by imparting memory into the bioabsorbable material components. The inventive apparatus and methods include increasing the radial expansion force of the stent through the use of a balloon within the stent delivery apparatus, substituting within the stent body one or more particularly rigid threads relative to the other threads, forming one or more of the helical threads of two side-by-side threads with one of the threads comprised of standard material and the other comprised of a more rigid material, attaching one or more bands to the stent body, and weaving circular or oval bands into the threads forming the wall of the stent shaped and positioned to resist axially elongation of the stent.

8 Claims, 6 Drawing Sheets

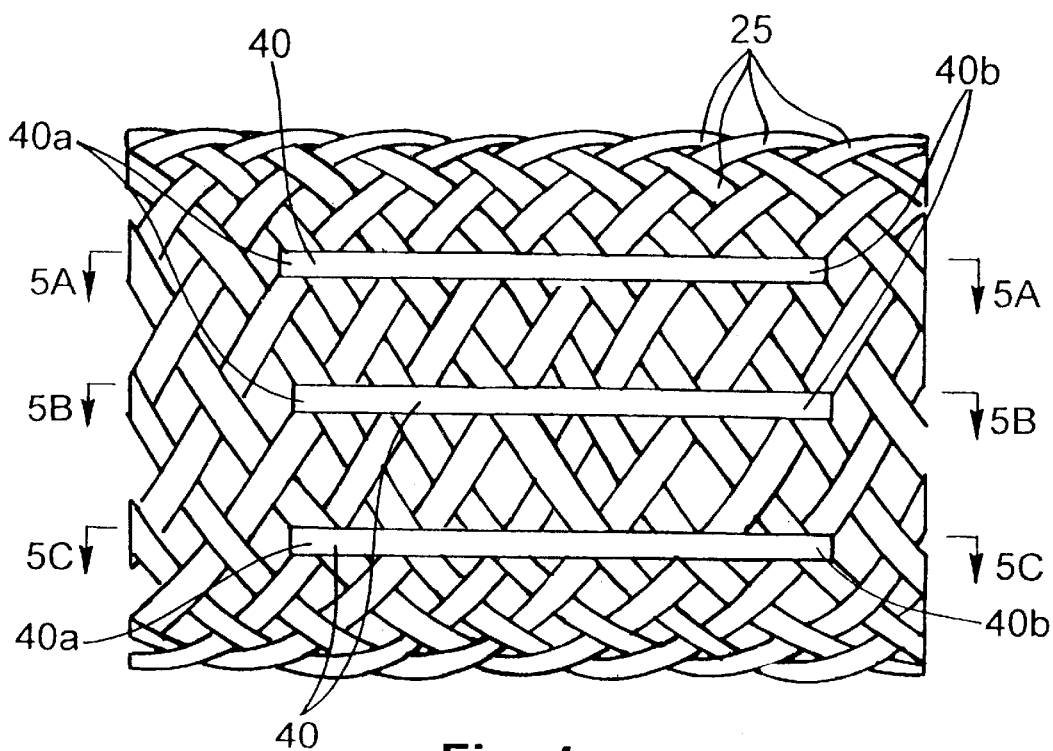
Fig. 4
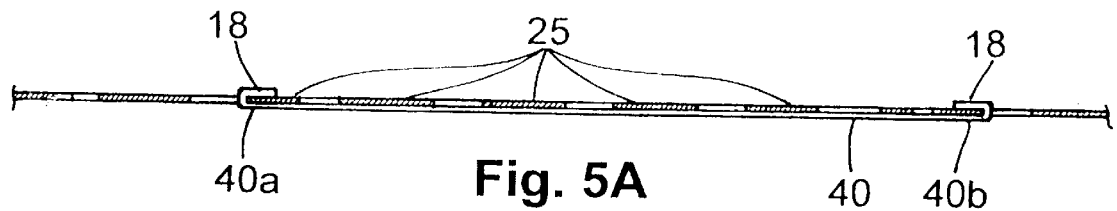
Fig. 5A
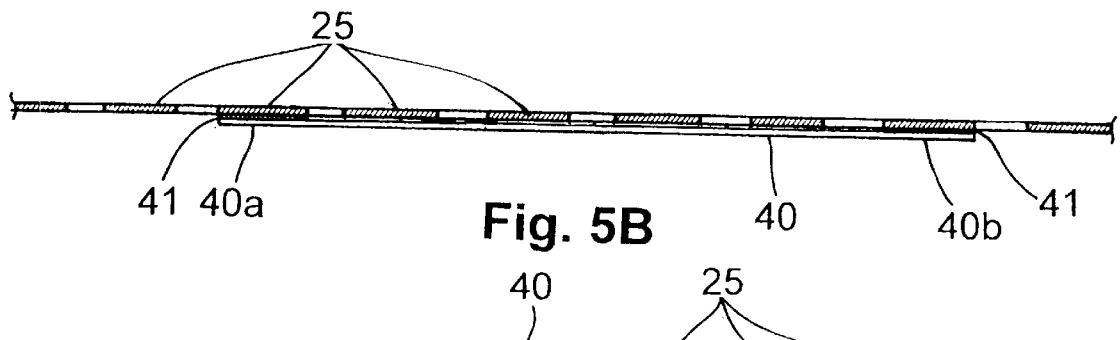
Fig. 5B
Fig. 5C

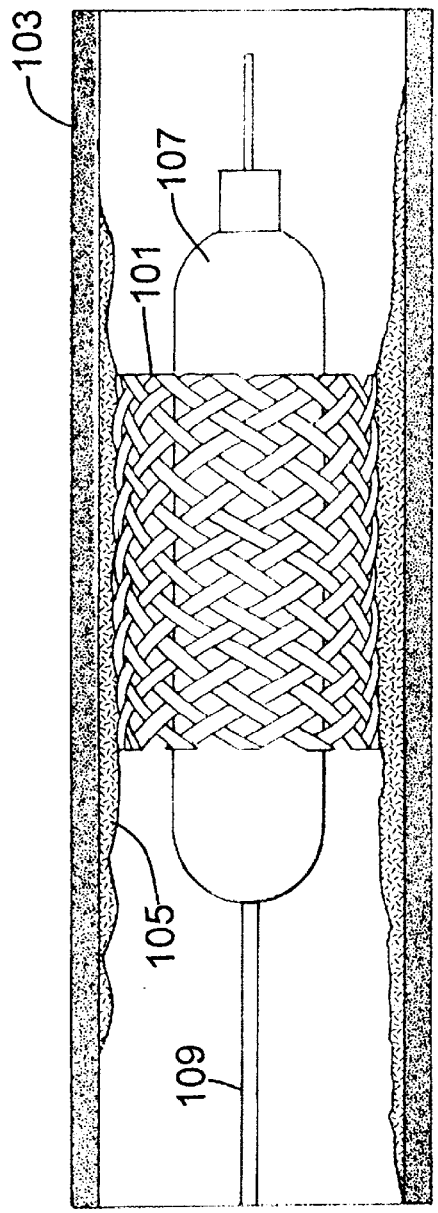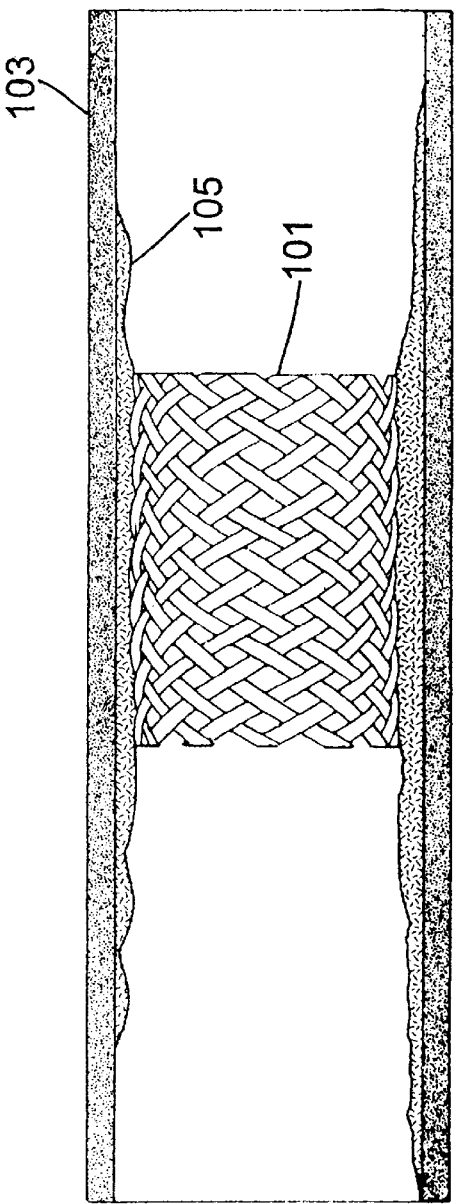

SELF-EXPANDING STENT WITH ENHANCED RADIAL EXPANSION AND SHAPE MEMORY

FIELD OF THE INVENTION

The invention pertains to stents and is particularly adapted to stents made from bioabsorbable materials.

BACKGROUND OF THE INVENTION

Self-expanding stents, such as braided or woven stents, for surgical implantation in body lumens (tubular vessels) are known for repairing or strengthening the vessels. A stent essentially is a hollow tube that may take the place or at least supplement the body vessel. With respect to the medical condition of stenosis, in which a body lumen tends to collapse or otherwise close, the stent supports the wall of the vessel to prevent it from collapsing or closing. A blood vessel that is narrowed due to the build up of intra-vascular plaque is one example of a stenosis. With respect to the medical condition of aneurism, in which a body lumen is weakened and cannot properly withstand the internal pressure within the vessel and bulges out or ruptures, the stent serves essentially the opposite function in that it substitutes for or supplements a weakened portion of the vessel. Stents are known for insertion in blood vessels, trachea, esophagus, urethra, ureter, nasal passages, ductal systems, etc.

Many different types of stents are commercially available at this time. Most stents need to be radially constricted, i.e., reduced in diameter, in order that they can be more easily inserted into the body lumen. Once they are in situ, the stent can be radially expanded to the desired diameter. Stents are known that are fabricated from rigid, but flexible materials that, when bent by force tend to retain the bent shape. Such stents may be inserted into the body lumen in an unstressed radially minimal shape while mounted over a deflated balloon. When the stent is in situ, the balloon is inflated in order to radially expand the stent, which will then retain the radially expanded shape after the balloon is deflated and removed.

Another type of stent is termed a self-expanding stent. Self-expanding stents may be woven in a variety of single or multiple strand woven designs which can be compressed radially, but will expand to its original shape once the constrictive force is removed. These woven designs are often made of shape memory materials, such as Nitinol, that expands when subjected to body temperature.

Another type of self-expanding stent is disclosed, for instance, in U.S. Pat. No. 1,205,743, issued to Didcott and incorporated herein by reference. Didcott discloses a braided, surgical dilator stent particularly adapted for esophageal dilation, but which can be adapted for use in other body vessels. This patent discloses a stent comprising a hollow tubular member the wall of which is formed of a series of individual flexible thread elements, each of which extends helically around the central longitudinal axis of the stent. A number of the flexible thread elements have the same direction of winding and are displaced relative to each other about the cylindrical surface of the stent. They cross a second plurality of helical thread elements which are also displaced relative to each other about the cylindrical surface of the stent, but having the opposite direction of winding. Accordingly, as shown in FIG. 1, the threads 12 of the first set of threads cross the threads 14 of the second set of threads at crossing points 16. FIG. 1 illustrates an embodiment in which the crossing threads are fully interlaced, however, it should be understood that the crossing threads may be interlaced at other frequencies, e.g., every other crossing point or every third crossing point.

As the stent is axially stretched, i.e., the longitudinal ends 18 and 20 are forced away from each other, the diameter reduces. Likewise, if the wall of the stent is constricted so as to reduce the stent's diameter, the stent elongates. In other words, radial constriction and axial elongation go hand in hand. When the force is released, the stent tends to spring back to its original diameter and length. The force with which the stent returns to its original state depends on many factors including the rigidity of the individual threads, the number of threads, and the original (resting) crossing angle a of the threads. The rigidity of the threads, in turn, depends upon such factors as the material out of which they are fabricated and the thickness of the threads. In general, the greater the rigidity and/or the greater the resting crossing angle of the threads, the greater the radial expansion force.

The desirable radial expansion force for a given stent depends on the application. When used in blood vessels, stents are commonly used to treat stenosis and particularly to hold the vessel open when it has become narrowed by either internal or external forces. Accordingly, such applications require relatively high radial expansion forces. Other applications, such as esophageal applications require much smaller forces.

U.S. Pat. No. 4,655,771 issued to Wallsten discloses a stent of the Didcott design particularly adapted for transluminal implantation in blood vessels for treating stenoses or aneurisms. In some applications, such as the esophageal application particularly discussed in the aforementioned patent to Didcott, the stent is temporary. In other applications, such as the blood vessel application discussed in the aforementioned Wallsten patent, the stent is permanent. In permanent installations, the tissue of the body lumen within which the stent is placed tends to grow around the stent such that the stent essentially becomes incorporated with the tissue of the body vessel and thus becomes permanently affixed. However, in the weeks or months before this occurs, the stent is held in position by friction between the outer surface of the stent body and the inner surface of the vessel created by the radial expansion force of the stent. Thus, the resting diameter of the stent, therefore, is selected to be slightly larger than the inner diameter of the vessel so that there is a constant force between the inner wall of the vessel and the outer wall of the stent.

Bioabsorbable stents are also known in the prior art. Bioabsorbable stents are manufactured from materials which, when exposed to body fluids, dissolve over an extended period of time. Thus, such stents are temporary in the sense that they will eventually dissolve and are eliminated from the body. Such stents are permanent, however, in the sense that there is no separate medical procedure needed to remove the stent from the body, it simply dissolves over time. Various bioabsorbable materials that are suitable for stents are known in the prior art including polymers such as poly-L,D-lactide, poly-L-lactide, poly-D-lactide, bioglass, poly(alpha hydroxy acid), polyglycolic acid, polylactic acid, polycaprolactone, polydioxanone, polyglucanate, polylactic acid-polyelethelene oxide copolymers, tyrosine derived polycarbonate, polyglycolide, modified cellulose, collagen, poly(hydroxybutyrate), polyanhydride, polyphosphoester, poly(amino acids) or combinations thereof. Vainionpää at al., Prog Polym. Sci., vol. 14, pp. 697–716 (1989); U.S. Pat. Nos. 4,700,704, 4,653,497, 4,649,921, 4,599,945, 4,532,928, 4,605,730, 4,441,496, and 4,435,590, all of which are incorporated herein by reference, disclose various compounds from which bioabsorbable stents can be fabricated.

Self-expanding braided stents rely on the spring force of the crossing threads that form the stent body as the radially expanding force. The magnitude of the radially expanding force is, therefore, a function of such factors as the number of threads, the size of the individual threads, the flexibility of the individual threads and the crossing angle of the threads. Self-expanding woven stents rely on a separate set of factors including size and number of threads employed, the flexibility of the individual threads, and the particular weave pattern chosen.

These characteristics of the stent, however, must be chosen based on factors in addition to the desired radial expansion force. For instance, the size of the threads is at least partially limited by the size of the lumen within which it will be employed. Further, characteristics of the material forming the stent body and thus the tensile strength and flexibility of the material is limited to materials which can be safely placed in a human body. Stents made from bioabsorbable materials exhibit different properties than corresponding metallic stent designs. Examples of properties that must be controlled when using bioabsorbable materials include degradation rates, material creep, and material position memory.

Accordingly, it is generally desirable to have various means by which to establish the radial expansion force of the stents. This is particularly true with respect to bioabsorbable stents due to the importance of final position memory associated with bioabsorbable materials.

Therefore, it is an object of the present invention to provide methods and designs to achieve optimum performance when employing bioabsorbable materials in stents.

It is another object of the present invention to provide a self-expanding stent with a supplemental mechanism for increasing the radial expansion force.

SUMMARY OF THE INVENTION

The invention applies fully to all stent designs, but is particularly adapted to stents that employ bioabsorbable materials, such as molded, braided and woven self-expanding bioabsorbable stents. The preferred embodiment of the invention comprises a radially self-expanding bioabsorbable stent comprised of a tubular body formed from a first plurality of flexible thread elements each extending in a helical configuration around the longitudinal axis of the stent body in a first direction of winding, a second plurality of flexible thread elements extending in a helical configuration around the longitudinal axis of the stent body having the opposite direction of winding, and a separate force applying mechanism associated with the stent body to axially constrict and/or radially expand the stent body.

In accordance with the helical thread structure of the stent body, the stent has a tendency to take a certain diameter and length. In use, the stent is first radially constricted (and axially elongated) in order to allow it to be more easily maneuvered into position in the body vessel. Once in situ, it is released such that it is allowed to radially expand (and axially constrict) back towards its rest diameter and length. Bioabsorbable polymer stents are subject to material memory effects, such that the amount of constrictive force and the degree of constriction can impart a memory to the stent that will alter the extent to which it will return to its original diameter and length.

Typically, the stent's final rest diameter is chosen to be slightly larger than the inner diameter of the body vessel within which it is placed so that the stent applies a radially outward force against the walls of the vessel tending to hold it in position by friction. The provision of a mechanism for imparting a larger radial diameter memory to the stent, or for supplementing the stent's radial expansion force increases the frictional force of engagement with the walls without the undesirable side effects of prior art means for increasing the radial expansion force, such as increasing the thickness or tensile strength of the threads, increasing the crossing angle of the threads, or increasing the number of threads.

The inventive mechanisms for increasing the radial expansion force include substituting within the stent body one or more particularly rigid threads relative to the other threads. Another mechanism is forming one or more of the helical threads of two side-by-side threads, one of the threads comprised of standard material and the other comprised of a more rigid material. Even further, one or more bands may be longitudinally attached at their ends to the stent body and their ends. The bands may be elastic or inelastic. The bands would tend to counteract any axially elongating force and/or apply an axially constrictive force. The bands may be attached at their ends to the helically wound threads by adhesive or by mechanical means, such as hooks.

In another embodiment, circular or oval bands are woven into the threads forming the wall of the stent. The bands may be elastic or inelastic. The bands are shaped and positioned to resist axially elongation of the stent.

In some embodiments, the longitudinal bands may be fabricated from a material that shrinks in length when exposed to moisture or body temperature. In other embodiments, the supplemental mechanism is fabricated of a bioabsorbable material such that, after an initial period when the extra radial expansion force is most needed, they dissolve and disappear. A primary benefit of increasing the radial expansion force of a bioabsorbable stent and causing an increase in the diameter of the stent in situ is that this larger diameter imparts memory into the stent. The final diameter achieved with self-expanding bioabsorbable stents is directly related, not only to the radial force generated by the stent design, but also the last diameter achieved immediately following stent delivery.

In accordance with another aspect of the present invention, the radial diameter memory of a bioabsorbable self-expanding stent with or without supplemental radial expanding mechanisms is adjusted by inserting the stent into a body vessel in conjunction with an inflatable balloon wherein inflation of the balloon when the stent is in the desired final position will impart a specific radial diameter memory to the stent by producing a temporary radial diameter greater than the stent body alone could create through its own self-expansion force. After some period of time, the balloon is deflated and withdrawn from the vessel.

BRIEF DESCRIPTION OF THE DRAWINGS

FIG. 4 is a plan view of a longitudinal portion of a bioabsorbable stent in accordance with a third embodiment of the present invention.

FIG. 5A is a cross sectional view of an exemplary stent taken along line 5A of FIG. 4 in accordance with one particular embodiment of the present invention.

FIG. 5B is a cross sectional view of an exemplary stent along line 5B of FIG. 4 in accordance with yet another embodiment of the present invention.

FIG. 5C is a cross sectional view of an exemplary stent along line 5C of FIG. 4 in accordance with yet another embodiment of the present invention.

FIG. 8D is a plan view of a portion of the stent of FIGS. 8A, 8B and 8C embedded in a body vessel after the balloon has been deflated.

FIG. 8E is a plan view of a portion of the stent of FIGS. 8A, 8B, 8C and 8D embedded in a body vessel after the balloon has been withdrawn.

DETAILED DESCRIPTION OF THE INVENTION

Figure 1:
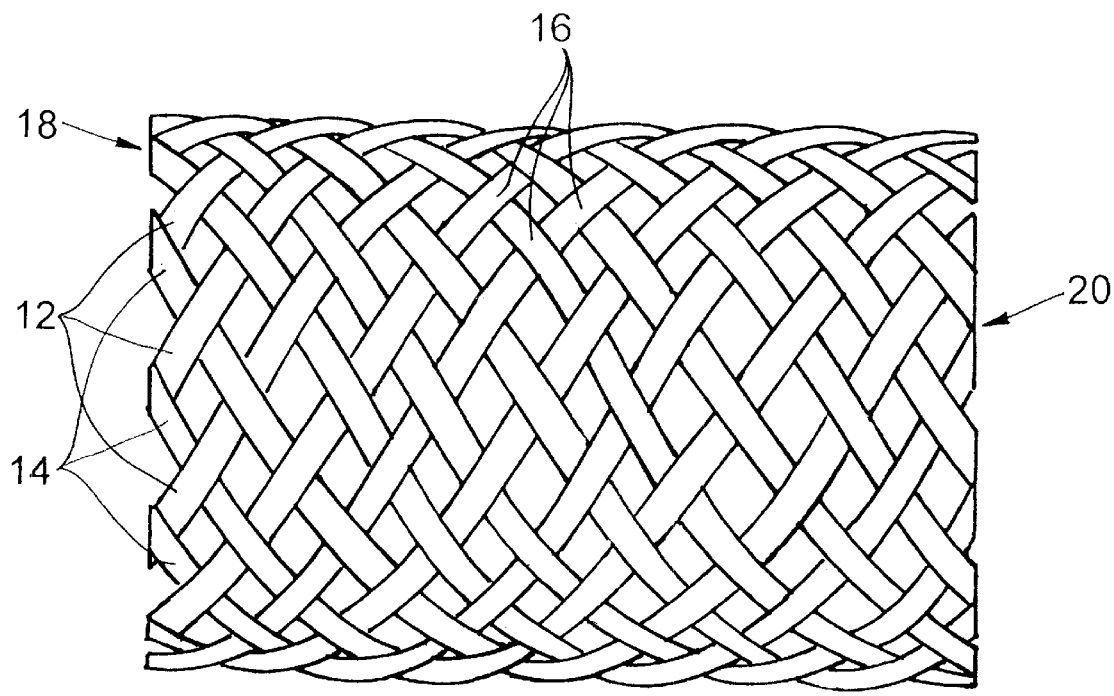
FIG. 1 is a plan view of a longitudinal portion of a stent in accordance with the prior art.
Figure 2:
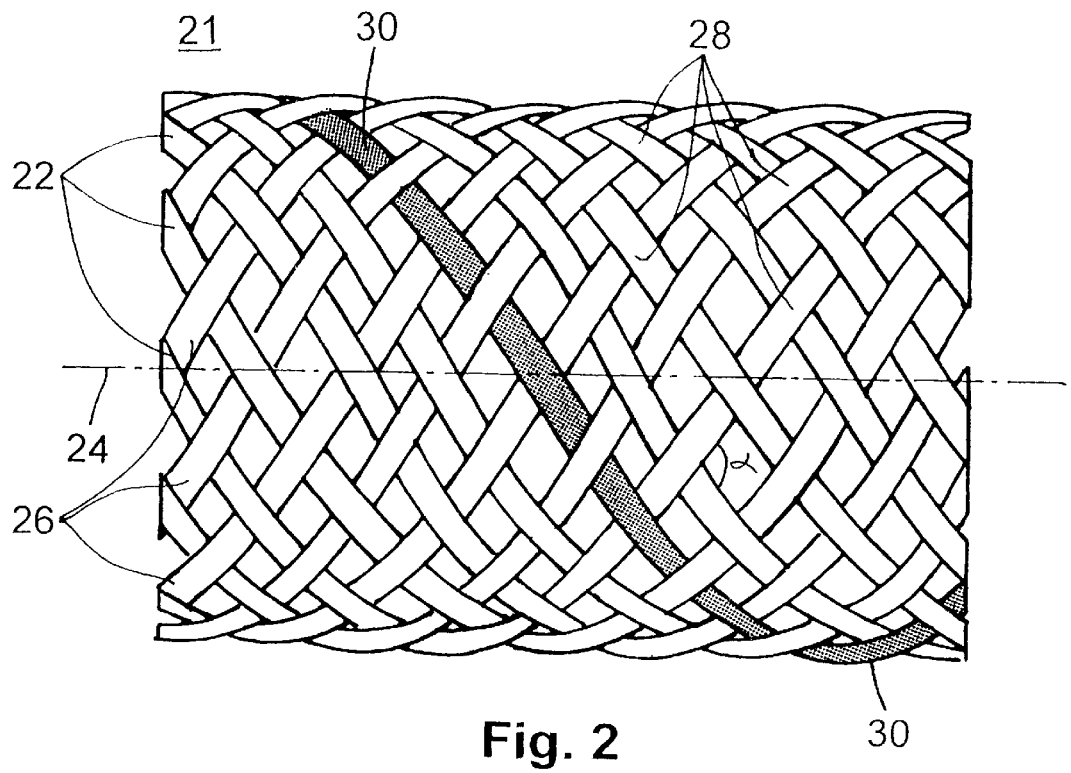
FIG. 2 is a plan view of a longitudinal portion of a bioabsorbable stent in accordance with a first embodiment of the present invention.

The invention is a stent for implantation in a body vessel such as a blood vessel, trachea, esophagus, urethra, ureter, nasal passage, ductal system, or any tubular passage. Specific design embodiments are disclosed for self-expanding braided or woven stent designs, however all stent designs that incorporate bioabsorbable materials exhibit the "memory" characteristics covered under the invention. FIG. 2 shows a stent 21 in accordance with a first embodiment of the present invention. As is known in the prior art, the stent body is primarily composed of a first set of threads 22 helically wound around the longitudinal axis 24 of the stent 21 and a second plurality of threads 26 helically wound in the opposite direction around the longitudinal axis 24 of the stent. The first and second sets of threads 22 and 26 cross each other at crossing points 28 having crossing angles a. The two sets of threads may or may not be braided with each other. The crossing threads may or may not be joined at the crossing points 18. The threads forming the stent body can be made of any suitable material, including, but not limited to bioabsorbable polymers such as polylactic acid or polyglycolic acid. In this specification, the term bioabsorbable will be used generically to refer to both bioabsorbable materials and bioresorbable materials to the extent that some groups of persons working in the relevant fields may make a distinction between the two terms.

As previously noted, stents of this type are self-expanding in that the diameter of such stents can be reduced and the length commensurately increased by applying either a radially restrictive force or a longitudinally lengthening force. When that force is removed, the stent tends to spring back towards its original diameter and length, but will retain a degree of size memory of the length and diameter to which it was altered. Also as previously noted, the magnitude of the size memory imparted into the stent, as well as the stent's radial expansion force depends on many factors, including the amount of diameter compression or length expansion placed on the stent, the length of time that the size of the stent was altered, the bioabsorbable material used, the rigidity of the threads, the thickness of the threads, the number of threads, and the crossing angle at rest of the threads.

Generally, the greater the crossing angle a at rest, the greater the radial expansion force. The magnitude of the expansion force is important for several reasons. For instance, the expansion force applied against the inner walls of the body vessel within which the stent is installed is the force that holds the stent in place until the tissue of the vessel can grow over and around the stent and thus permanently affix the stent within the vessel. Further, in many applications, the very purpose of the stent is to hold the vessel open and thus the final size memory given to the stent, and the proper magnitude of radial expansion force is critical. In some applications, such as installation in blood vessels, the expansion force needs to be relatively great to hold open the vessel. In others, such as esophageal applications, the force must be considerably less.

In many applications, it may be desirable to supplement the radial expansion force inherently provided by this type of bioabsorbable stent design. For instance, the size of the vessel and/or the route through which the stent must be inserted may dictate that the threads be thin or of a certain number that is insufficient to provide the desired radial expansion force, or the degree to which the stent must be compressed for insertion could impart such reduced radial memory to the stent as to prevent its full expansion.

FIG. 2 discloses a first mechanism for supplementing the radial expansion force of the stent. One or more of the threads 30 may be made of a different material or thickness than the other threads whereby that thread is more rigid than the other threads and thus exerts a greater radial expansion force.

Figure 3:
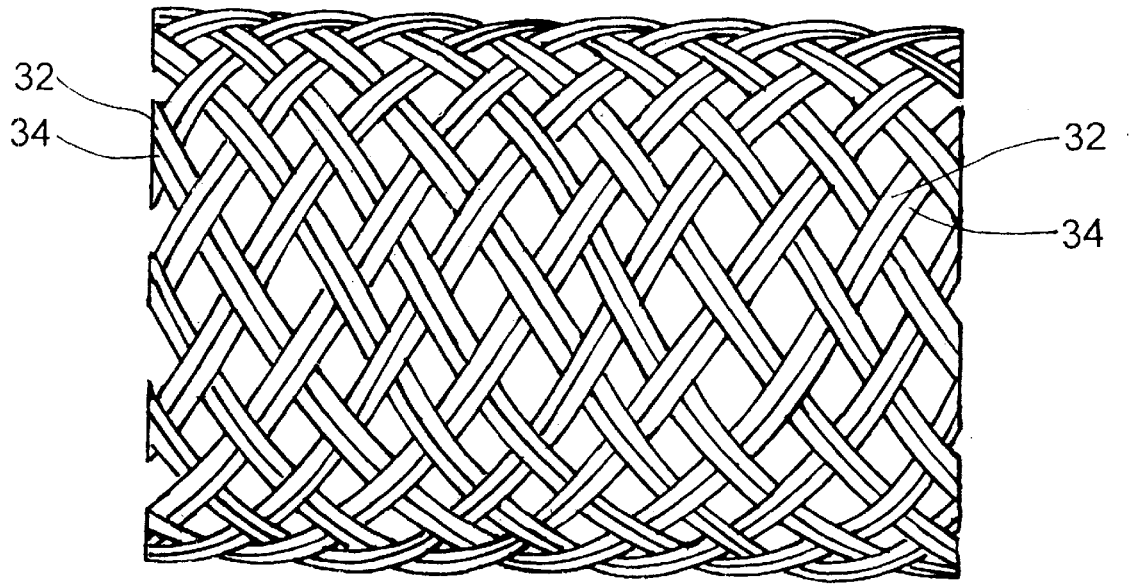
FIG. 3 is a plan view of a longitudinal portion of a bioabsorbable stent in accordance with a second embodiment of the present invention.

FIG. 3 shows a variation on this mechanism in which one or more of the bioabsorbable threads forming the stent body are replaced with two side-by-side threads 32 and 34. One of the two threads 32 forming each pair or threads is of a standard design, while the other is fabricated of a different material or thickness so that it is more rigid and thus exerts a greater radial expansion force.

It should be understood by those of skill in the art that the greatest need for radial expansion force exists at the moment of insertion and/or for a short period of time thereafter (usually days, weeks or months). Specifically, after a certain period of time, the tissue of the vessel within which the stent is installed grows around the stent, thus more fixedly attaching the stent within the vessel. However, in the first days or weeks, before the tissue has a chance to grow around the stent, the stent relies primarily or exclusively on the friction created by the radial expansion force of the stent against the inner wall of the vessel. Accordingly, the supplemental threads 30 and 34, respectively, in the embodiments of FIGS. 2 and 3 are also made of bioabsorbable material that will dissolve over time. Preferably, the rate at which these threads 30 and 34 dissolve is commensurate with the expected rate of tissue growth over the stent. In embodiments where the threads forming the main stent body are bioabsorbable themselves, the supplemental threads 30 and 34 are preferably bioabsorbed at a faster rate than the main stent body threads.

In alternate embodiments, the supplemental threads do not necessarily need to "replace" normal threads but simply may be woven into the design as extra threads. The supplemental threads may be inside the stent, outside the stent or integrated into the stent braid.

FIG. 4 shows an alternate mechanism for supplementing radial expansion force. In this particular embodiment, the radial expansion force is supplemented by longitudinal strips or bands 40 attached to the helically wound threads that form the wall of the stent and which apply increased longitudinally constricting force, which, of course, increases the radial expansion force. These longitudinal strips or bands 40 are attached at or near their ends 40a, 40b to the stent and tend to force the stent body to shorten in length. The ends 40a, 40b may be hooked onto the threads or adhered by an adhesive to the stent body. FIG. 5A is a cross sectional view of an exemplary stent taken along line 5A of FIG. 4 in accordance with one particular embodiment of the present invention in which hooks 18 at the ends 40a and 40b of the strips hook over the threads 25. FIG. 5B is a cross sectional view of an exemplary stent taken along line 5B of FIG. 4 in accordance with another embodiment of the present invention in which the ends 40a, 40b of the strips 40 are adhered by an adhesive 41 to the stent body.

FIG. 5C is a cross sectional view of an exemplary stent taken along line 5C of FIG. 4 in accordance with yet another embodiment of the present invention in which the bands 40 form a continuous band around the stent body such that the bands are essentially trapped within the braiding of the stent itself.

In a preferred embodiment, the strips or bands are elastic. During insertion, the entire stent body, including the bands, are longitudinally stretched. When the stent is released from the insertion apparatus, the stent under its own force as well as the supplemental force applied by the tendency of the strips or bands to constrict back to their rest position provides radial expansion force against the walls of the vessel within which it is inserted. These bands may be positioned on the outside of the stent wall, on the inside of the stent wall or woven among the threads of the stent wall.

In another preferred embodiment of the invention, the supplemental strips or bands 40 are fabricated of a material that shrinks in length when exposed to moisture or body temperature. The shrinkage of the bands 40 will apply a longitudinally constricting and, therefore, radially expansive, force on the stent. Materials that have these properties and that are compatible with insertion into the body are well known and include polylactic and polyglycolic acid, which can be adjusted in their amounts and force of shrinkage through processing, including orientation of their molecular structure.

As discussed above, the threads forming the main stent body as well as the supplemental bands may be fabricated of a bioabsorbable material. In a preferred embodiment, the bands or other supplemental radial expansion mechanism have a higher bioabsorption rate than the main stent body threads.

Figure 6:
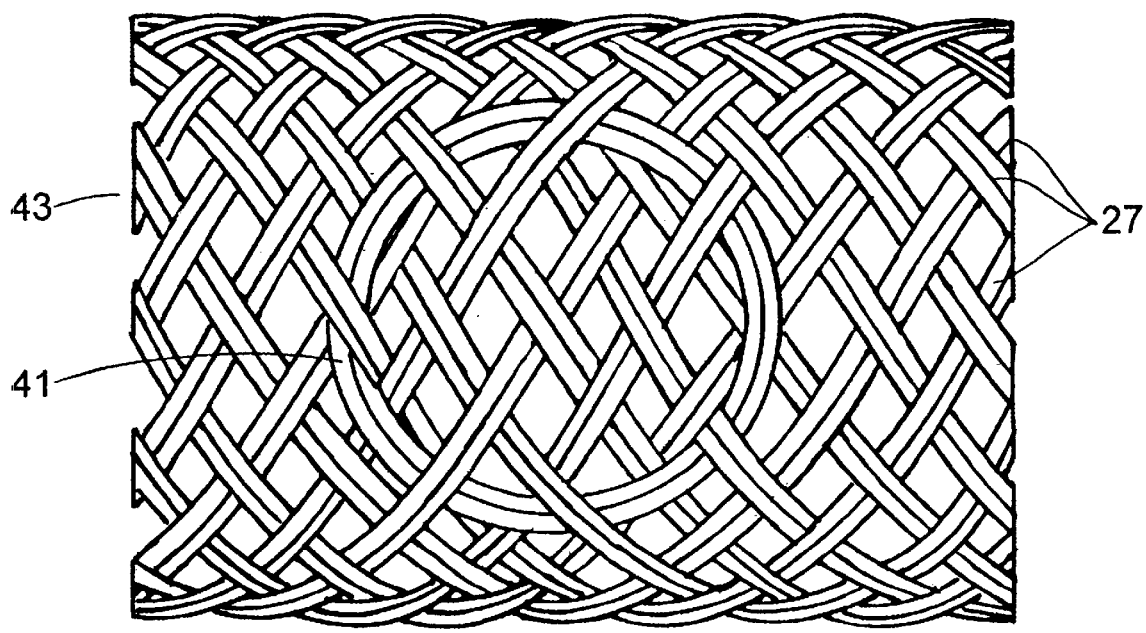
FIG. 6 is a plan view of a longitudinal portion of a stent in accordance with another embodiment of the present invention.

FIG. 6 shows another embodiment of the invention in which loops 41 are integrated into the stent body 43 by weaving into the threads 27 forming the stent body 43 in a different manner than in the FIG. 4 embodiment. Particularly, each supplemental loop 41 forms a continuous loop which is woven into the body 43 of the stent itself. When the stent is elongated, the loop 41 is elongated and exerts a force tending back towards its original shape thus resisting elongation of the stent body. This longitudinally restricting force, of course, exerts a radially expansive force to the stent. While, for sake of clarity, FIG. 6 shows only one of these loops 41. In a preferred embodiment, two, three or more loops 41 may be incorporated into the stent body arranged radially around the wall. Thus, for instance, four loops may be arranged at 90° intervals around the radial periphery of the stent body as illustrated in FIG. 7 (in which only three of the bands are visible).

Figure 7:
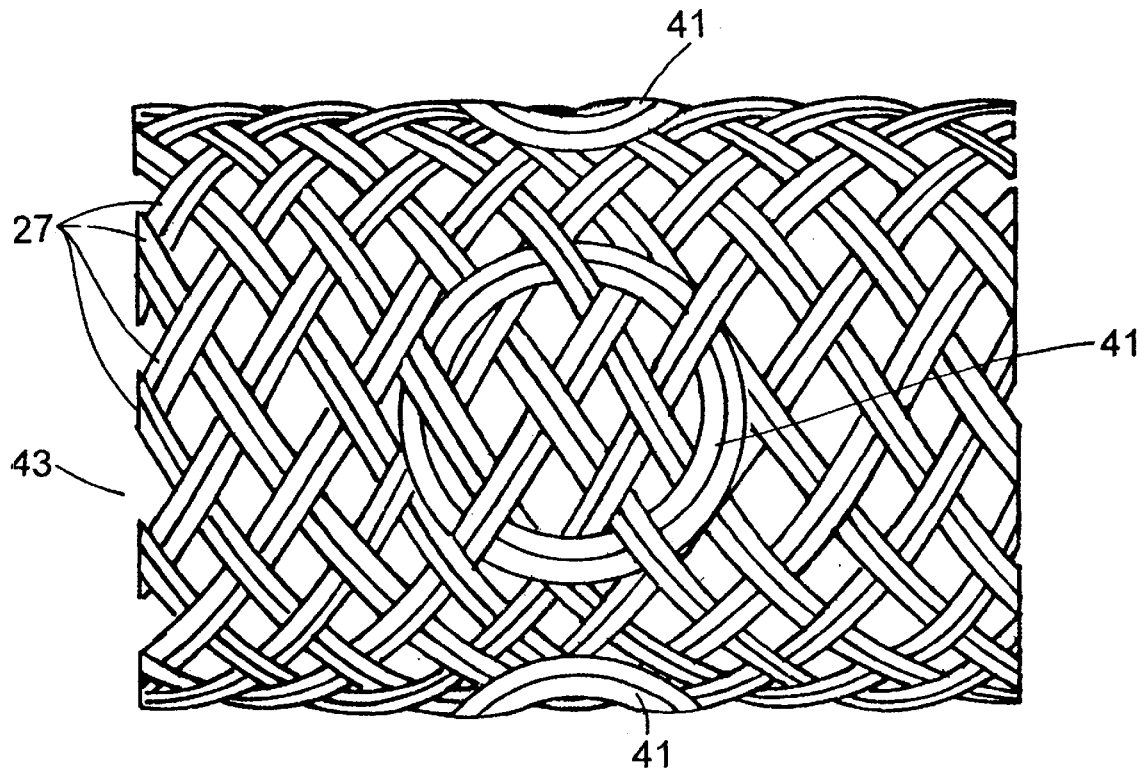
FIG. 7 is a plan view of a stent in accordance with another embodiment of the present invention.

In FIGS. 6 and 7, the threads 27 of the stent body as well as the supplemental loops 41 are illustrated as double threads like those discussed above in connection with the embodiment of FIG. 3. However, it should be understood that the supplemental loops 41 and/or the threads 25 forming the stent body 43 can be single strand threads such as threads 28 and 25 illustrated in connection with the embodiments of FIGS. 2 and 4 above.

In accordance with the previously discussed issue of material memory, a self-expanding bioabsorbable stent with or without the supplemental radial expansion force means previously disclosed in this specification may be placed in the body with the assistance of an inflatable balloon to impart final diameter memory to the stent. Systems are available in the prior art for inserting non-self-expanding metallic stents using an insertion apparatus in which the stent is mounted on an inflatable balloon and then inflating the balloon to expand the stent when the desired destination position in the vessel has been reached. It is also known in the prior art to insert radially self-expanding metallic stents with a standard insertion apparatus, to remove the insertion apparatus, and then to insert a balloon into the vessel to a position within the stent and then expand the balloon to radially stretch the stent even further in order to more securely embed it within the vessel, and then remove the balloon.

In accordance with the present invention, the bioabsorbable stent is itself inserted using an insertion apparatus which includes an inflatable balloon positioned adjacent to (including surrounding) the radially constricted/axially elongated stent. When the stent is in the final destination position, the balloon is inflated to expand the stent to a diameter larger than its final resting diameter, thereby imparting a diameter size memory to the stent that will supplement the stent's natural self-expansion force. The balloon is then deflated and the insertion apparatus, including the balloon, is removed from the vessel.

Insertion apparatuses are available in the prior art for inserting non-self-expanding metallic stents in the body and expanding them. However, such delivery devices for non-self-expanding stents would not work in connection with a self-expanding stent because of the tendency of self-expanding stents to radially expand. Particularly, a mechanism must be provided that holds the stent in a radially constricted shape until the stent is delivered to the final release location in the body.

Figure 8A:
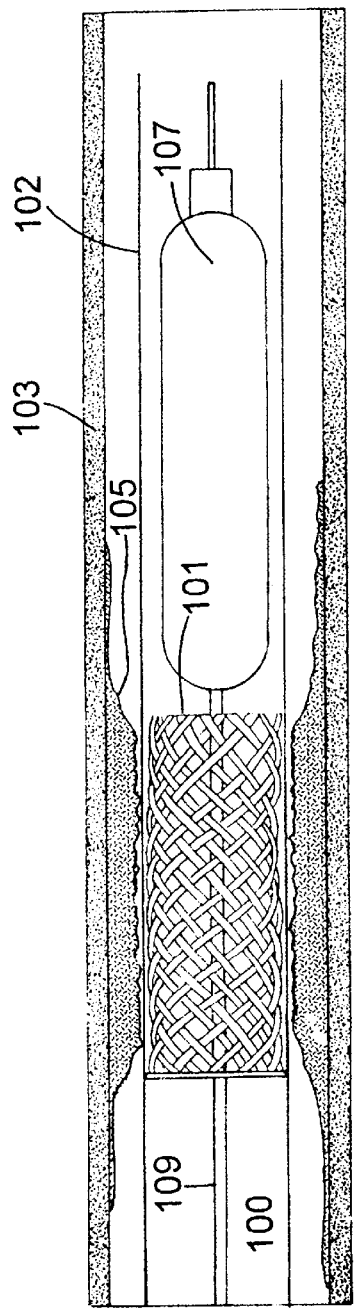
FIG. 8A is a view of the stent prior to delivery into a vessel, with a delivery catheter, an inflation balloon, and a retractable over-sheath that acts to constrain both the dilation balloon and the stent until the time of stent release.
Figure 8B:
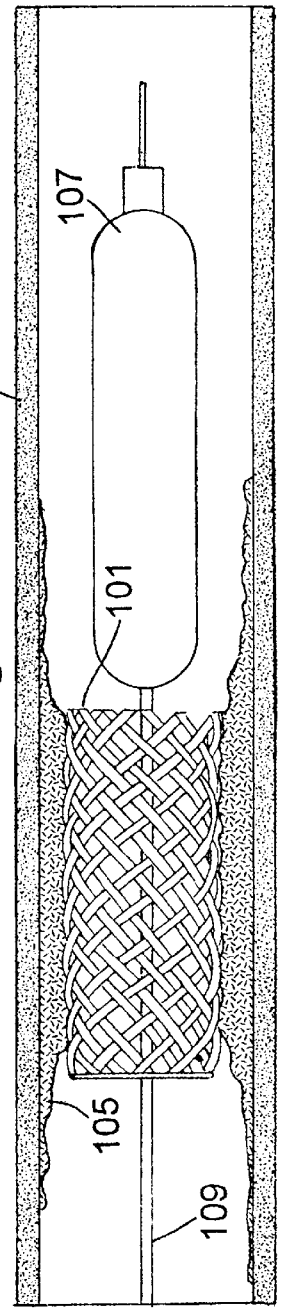
FIG. 8B is a plan view of a portion of the stent and inflatable balloon combination after the initial release of the stent into a body vessel, and prior to expansion of the balloon.
Figure 8C:
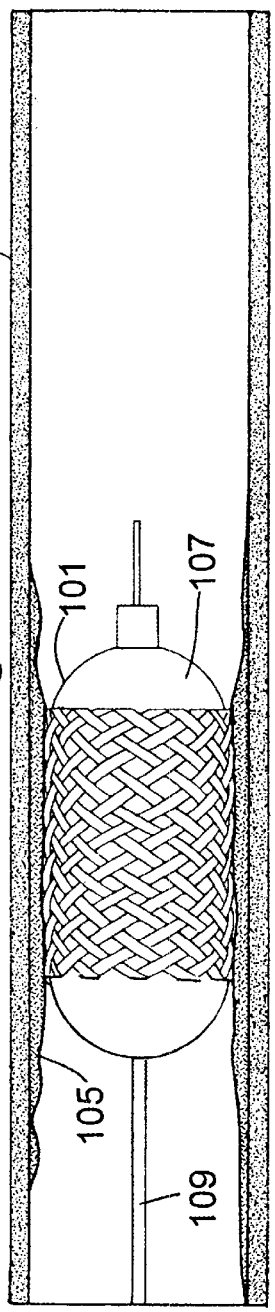
FIG. 8C is a plan view of a portion of the stent and inflatable balloon combination of FIG. 8A in a body vessel after inflation of the balloon.

FIGS. 8A, 8B, 8C, 8D and 8E illustrate the progression during insertion of such a stent. FIG. 8A is a view of the delivery system 100 prior to release of the stent into a body lumen 103. The stent 101 and balloon 107 are mounted on a delivery catheter 100 that is inserted into the lumen and guided to the location at which it is to be deployed which, in this example, is a stenosis 105. The delivery catheter 100 preferably comprises a retractable over sheath 102 and an inner shaft 109 through which a gas or liquid can be delivered to the internal space of the balloon 107 in order to inflate it. Preferably, the balloon 107 and the stent 103 are arranged in tandem (one behind the other) in order to minimize the diameter of the catheter delivery system 100. However, in alternate embodiments, the stent 103 can be initially positioned surrounding the balloon 107. The inner shaft 109 includes an annular ring 106 immediately adjacent the distal end of the stent 103 that will prevent the stent from being drawn along with the outer sheath 102 when the outer sheath is retracted. Once the stent 103 has been positioned proximal the stenosis 105, the outer sheath 102 is retracted to release the stent and allow it to radially expand and engage the walls of the lumen (or the stenosis) as shown in FIG. 8B. Once the stent 103 is released, the balloon 107 can be drawn back to a position within the stent and then inflated as shown in FIG. 8C. The stent will not move when the balloon is drawn back because the stent is expanded at this point and is frictionally engaged with the wall of the lumen or stenosis. Also, it is larger than the balloon such that the balloon should not even contact the stent as it is drawn back within the stent.

The inflated balloon further radially expands the stent 101 and imparts a shape memory to the stent of a diameter larger than prior to inflation. In FIG. 8D, the balloon 107 has been deflated and the increased diameter memory has been imparted to the stent. The stent 101 remains at a diameter greater than the diameter that it would have reached had it simply been inserted and released without the additional diameter memory imparted by the balloon 107 during insertion. In FIG. 8E, the insertion apparatus 100 including the balloon 107 has been removed leaving the expanded stent 101 in place in the lumen 103 helping hold the stenosis 105 open.

Having thus described a few particular embodiments of the invention, various alterations, modifications, and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

I claim:
1. A self-expanding stent comprising:
   a stent body in the shape of a tube and formed of a bioabsorbable material; and
   an elastic member fixed to said stent body at first and second locations longitudinally displaced from each other along said stent body for exerting a radial expansion force in addition to a radial force of the stent body and to impart a memory into the stent;
   wherein said elastic member is attached to said stent body by adhesive.
2. The stent of claim 1 wherein said stent body comprises a first set of threads helically wound in a first direction and a second set of threads helically wound in a second direction wherein said first set of threads and said second set of threads cross each other.
3. The stent of claim 1 wherein said stent body is comprised of at least one woven thread.
4. The stent of claim 1 wherein said means for exerting a force is formed of a bioabsorbable material.
5. The stent of claim 1 wherein said elastic member is permanently affixed to said stent body and is formed of a bioabsorbable material.
6. The stent of claim 5 wherein said bioabsorbable material of said stent body has a rate of bioabsorption that is slower than a rate of bioabsorption of said means for exerting.
7. The stent of claim 1 wherein said elastic member is formed of a material that shrinks when exposed to body temperature or moisture.
8. A self-expanding stent comprising:
   a stent body in the shape of a tube and formed of a bioabsorbable material;
   means for exerting a radial expansion force in addition to the radial expansion force of the stent body and to impart memory into the stent body, wherein said means for exerting a radial expansion force is formed of a bioabsorbable material having a rate of bioabsorbtion that is faster than a rate of bioabsorbation of said bioabsorbable material of said stent body.

* * * * *